(12) United States Patent
Iwase et al.

(10) Patent No.: US 9,192,729 B2
(45) Date of Patent: Nov. 24, 2015

(54) LIQUID INJECTOR

(71) Applicant: Terumo Kabushiki Kaisha, Tokyo (JP)

(72) Inventors: Yoichiro Iwase, Kanagawa (JP); Junichi Ogawa, Shizuoka (JP); Kouichi Tachikawa, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/224,857

(22) Filed: Mar. 25, 2014

(65) Prior Publication Data

US 2014/0207077 A1    Jul. 24, 2014

Related U.S. Application Data

(63) Continuation of application No. PCT/JP2012/067581, filed on Jul. 10, 2012.

(30) Foreign Application Priority Data

Sep. 26, 2011    (JP) ................. 2011-209642

(51) Int. Cl.
*A61M 5/32*    (2006.01)
*A61M 5/20*    (2006.01)

(52) U.S. Cl.
CPC ............ *A61M 5/3202* (2013.01); *A61M 5/32* (2013.01); *A61M 2005/2013* (2013.01)

(58) Field of Classification Search
CPC ................. A61M 5/2033; A61M 2005/206; A61M 2005/2013; A61M 2005/208
USPC .................. 604/110, 117, 135, 192, 197, 198
See application file for complete search history.

(56) References Cited

U.S. PATENT DOCUMENTS

| 5,041,094 A | * | 8/1991 | Perego et al. .............. 604/143 |
| 6,102,896 A | * | 8/2000 | Roser ........................ 604/218 |
| 2004/0171991 A1 | | 9/2004 | Cherif-Cheikh | |

(Continued)

FOREIGN PATENT DOCUMENTS

| JP | 2004-526552 A | 9/2004 |
| JP | 2007-215863 A | 8/2007 |

(Continued)

OTHER PUBLICATIONS

International Search Report dated Sep. 4, 2012 received in International Application No. PCT/JP2012/067581.

*Primary Examiner* — Nicholas Lucchesi
*Assistant Examiner* — Gerald Landry, II
(74) *Attorney, Agent, or Firm* — Foley & Lardner LLP

(57) ABSTRACT

A liquid injector comprises a contact member comprising a tube body including an opening located at a distal end of the contact member; an inner structure body comprising: a cylindrical main body; and a hollow needle, wherein the inner structure body is movable to (i) a first position at which a needle tip is located proximal of the opening, and (ii) a second position at which the needle tip is located distal of the opening; and a regulating member detachably mounted on the inner structure body, including a fixing portion to be fixed to the contact member at the second position. When the inner structure body moves to the second position from the first position and returns to the first position again, the regulating member is fixed to the contact member with the fixing portion at the second position, separated from the inner structure body, and stays at a position at which the regulating member covers at least part of an area of the opening.

15 Claims, 9 Drawing Sheets

(56) References Cited

U.S. PATENT DOCUMENTS

| | | | |
|---|---|---|---|
| 2006/0079834 A1* | 4/2006 | Tennican et al. | 604/88 |
| 2008/0077093 A1 | 3/2008 | Gratwohl et al. | |
| 2008/0195056 A1* | 8/2008 | Bishop et al. | 604/218 |
| 2008/0228147 A1* | 9/2008 | David-Hegerich et al. | 604/198 |
| 2009/0318864 A1* | 12/2009 | Carrel et al. | 604/117 |
| 2010/0228226 A1 | 9/2010 | Nielsen | |
| 2011/0301548 A1* | 12/2011 | Young | 604/200 |
| 2012/0116319 A1* | 5/2012 | Grunhut | 604/198 |
| 2013/0096512 A1* | 4/2013 | Ekman et al. | 604/197 |
| 2013/0317448 A1* | 11/2013 | Hourmand et al. | 604/197 |

FOREIGN PATENT DOCUMENTS

| | | |
|---|---|---|
| JP | 2008-062063 A | 3/2008 |
| JP | 2011-509097 A | 3/2011 |
| WO | WO-2010/112521 A1 | 10/2010 |

* cited by examiner

LIQUID INJECTOR

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/067581 filed on Jul. 10, 2012, which is based upon and claims the benefit of priority of Japanese Application No. 2011-209642 filed on Sep. 26, 2011, the entire contents of which are hereby incorporated by reference in their entireties.

BACKGROUND

1. Technical Field

The present disclosure relates to a liquid injector.

2. Background Art

When blood collection or administration of medicinal solution is performed to a patient, a blood vessel of the patient is punctured with a hollow needle. A known medical device whereby the above-mentioned procedure can be performed is a medical device including a cylindrical (tubular) main body and a hollow needle supported inside the main body (see, for example, JP 2007-215863 A).

According to the medical device disclosed in JP 2007-215863 A, the hollow needle is retractable with respect to the main body of the medical device. More specifically, a needle tip is movable to a first position located inside the main body of the medical device and to a second position where the needle tip is projected from the main body of the medical device. The hollow needle moves to the second position at the time of puncture. The hollow needle moves to the first position after puncture.

However, according to the medical device disclosed in JP 2007-215863 A, there is a problem in which a part of an operator's fingertip may enter the inside from a distal-end opening of the main body of the medical device and the needle tip of the hollow needle located at the first position may puncture the operator's fingertip after using the medical device, depending on a size of the distal-end opening of the main body of the medical device or an extent of retraction of the hollow needle with respect to the main body of the medical device.

Thus, there is a need for a liquid injector in which erroneous puncturing with a needle tip of a finger or the like can be reliably prevented after puncturing a living body surface with the needle tip of a hollow needle.

SUMMARY OF INVENTION

In one embodiment, a liquid injector includes: a living body contact member formed of a tube body including an opening opened at a distal end and having an edge portion of the opening placed on a living body surface; an inner structure body including: a main body disposed inside the living body contact member, formed cylindrical, and having an internal cavity filled with liquid; and a hollow needle disposed on a distal-end portion of the main body, communicating with the main body and including a sharp needle tip at the end, wherein the inner structure body is supported movably to a first position where the needle tip is located closer to the proximal-end side than the opening and to a second position where the needle tip is projected more to the distal-end side than the opening so as to puncture a living body surface while the living body contact member is placed on the living body surface; and a regulating member detachably mounted on the inner structure body, movable together with the inner structure body in the mounted state, and including a fixing portion to be fixed to the living body contact member at the second position. When the inner structure body moves to the second position from the first position and returns to the first position again, the regulating member is fixed to the living body contact member with the fixing portion at the second position, simultaneously separated from the inner structure body, and stays at the position to cover at least a part of the vicinity of the opening.

In one aspect, the regulating member covers at least a part of the vicinity of the opening closer to a proximal-end side than the opening.

In one aspect, the regulating member is formed in a ring shape and an inner diameter of the regulating member is a size enough to regulate entry of a fingertip.

In one aspect, the living body contact member includes a projected portion projected from an inner peripheral portion halfway in an axial direction of the living body contact member, and the fixing portion is configured to grip the projected portion from a distal-end side and a proximal-end side.

In one aspect, the regulating member has a function to regulate the inner structure body that has returned again to the first position so as not to move again to the second position.

In one aspect, the main body includes a wedge portion projected to an outer peripheral portion of the main body and having a width gradually increasing in the distal end direction from a side view, and the regulating member is formed in a ring shape and having a wall portion on which a discontinuous portion is formed, and the discontinuous portion allows the wedge portion to pass in a direction to the first position when the inner structure body returns again to the first position while the discontinuous portion inhibits the wedge portion from passing in an opposite direction.

In one aspect, the inner structure body includes a gasket slidable inside the main body, and a pusher connected to the gasket and configured to move and control the gasket.

In one aspect, the liquid injector further includes a gripping member which is disposed on an outer peripheral side of the inner structure body and configured to be gripped when the inner structure body is moved and controlled.

In one aspect, the liquid injector further includes a biasing member configured to bias the inner structure body in the proximal-end direction.

DETAILED DESCRIPTION

In the following, a liquid injector according to embodiments of the present invention will be described based on a preferable embodiment illustrated in the attached drawings.

Figure 5:
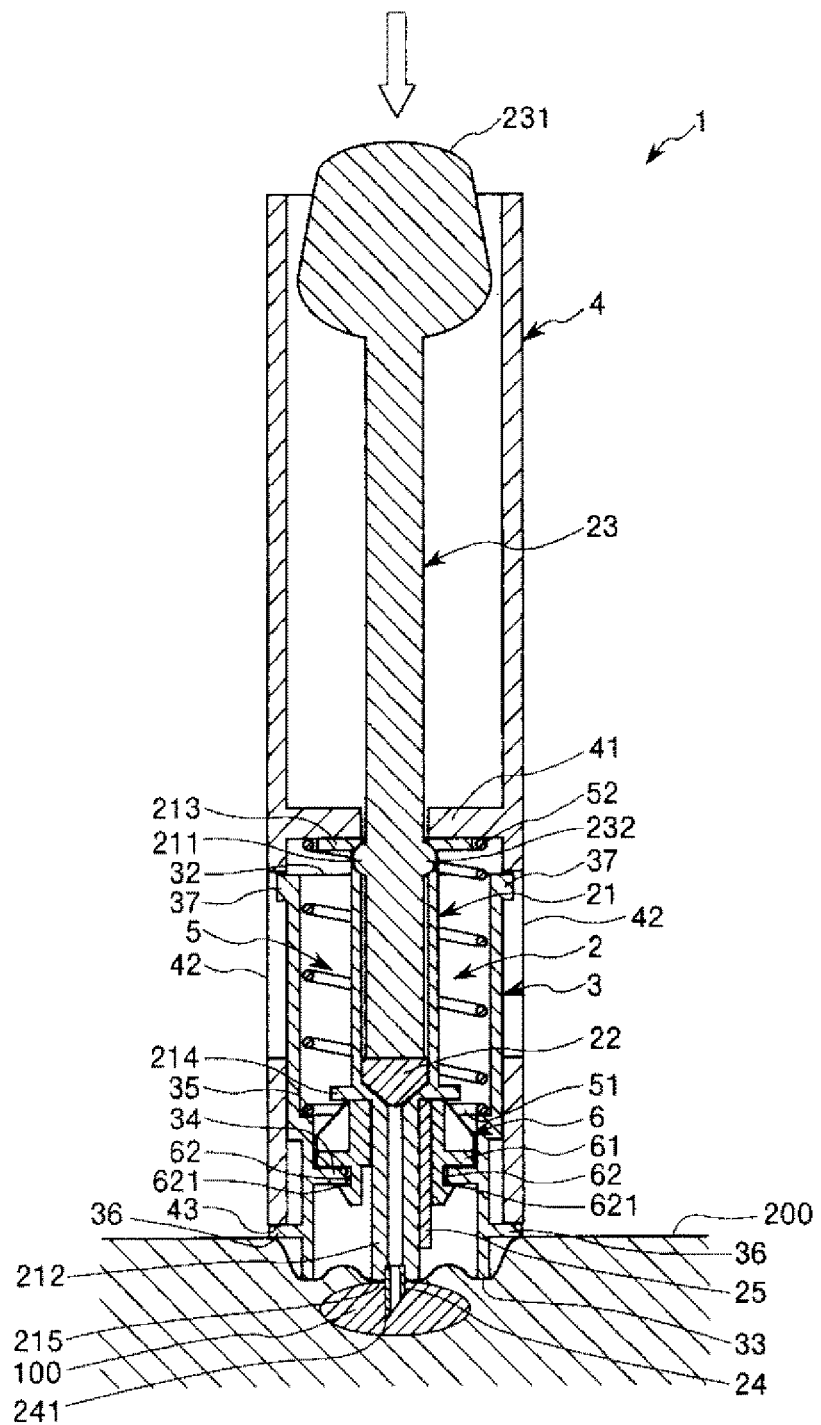
FIG. 5 is a longitudinal sectional view illustrating the using state of the liquid injector in order according to the present invention.
Figure 6:
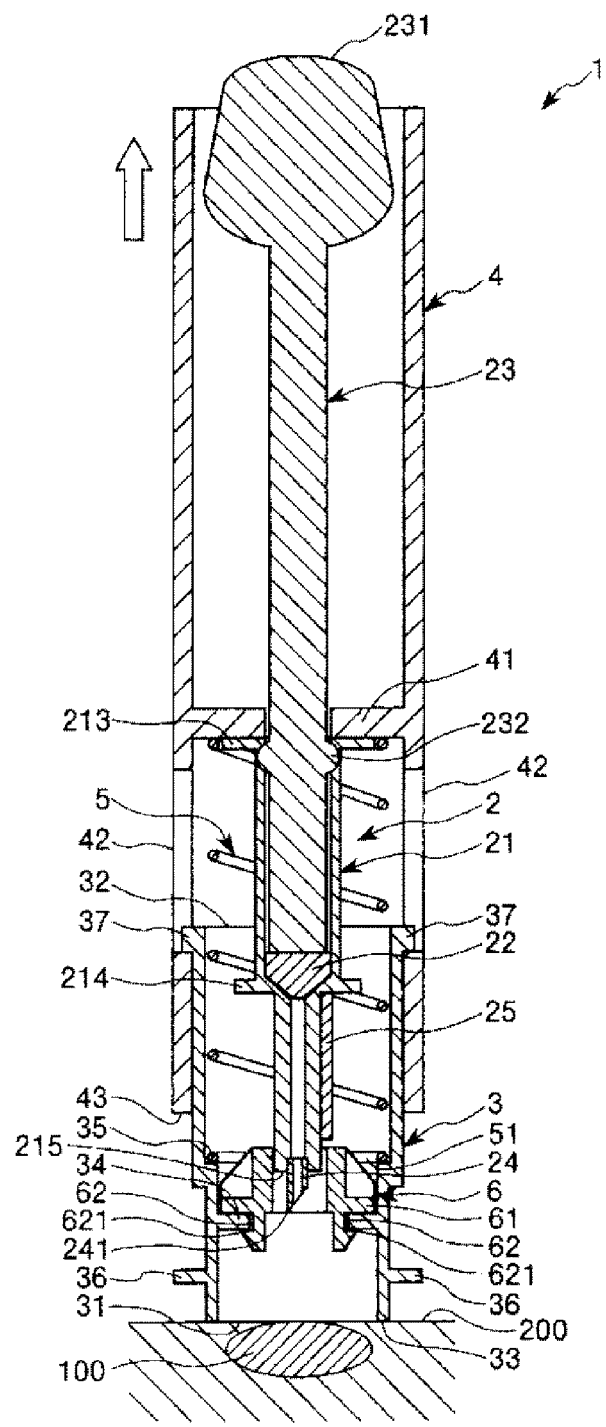
FIG. 6 is a longitudinal sectional view illustrating the using state of the liquid injector in order according to the present invention.
Figure 7:
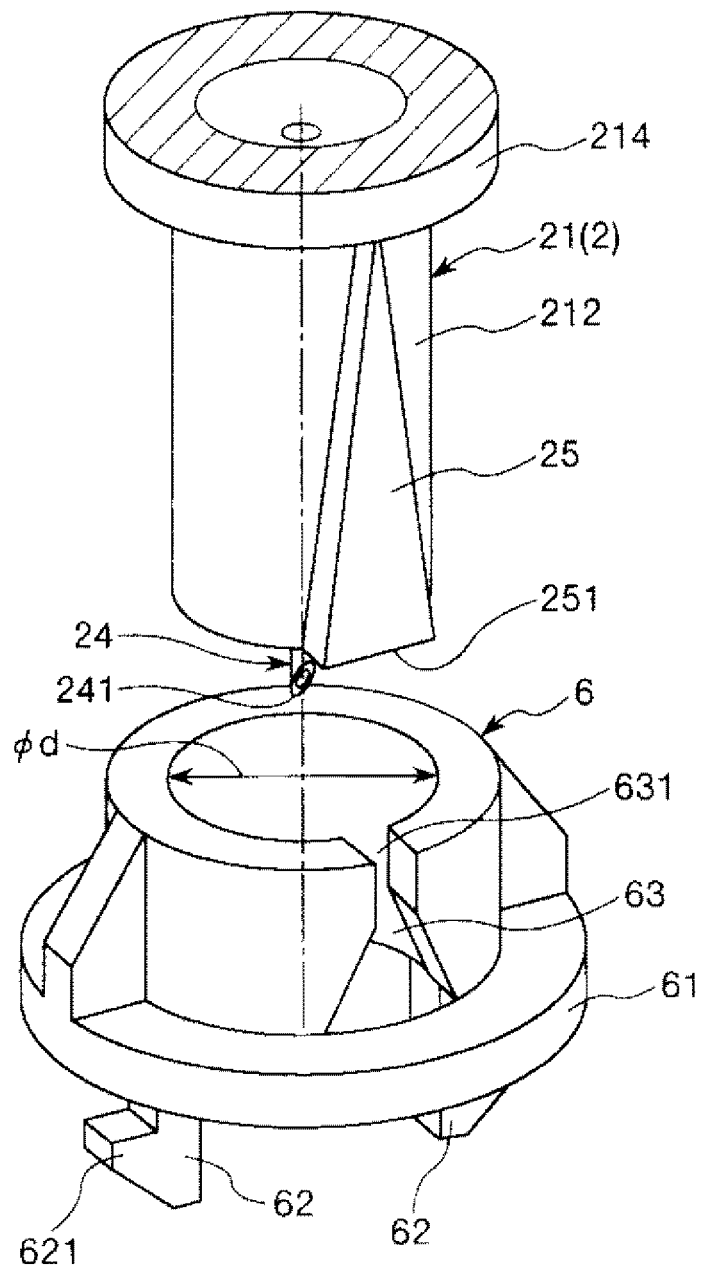
FIG. 7 is an exploded perspective view illustrating a main body and a regulating member in the liquid injector illustrated in FIGS. 1 to 6.
Figure 8:
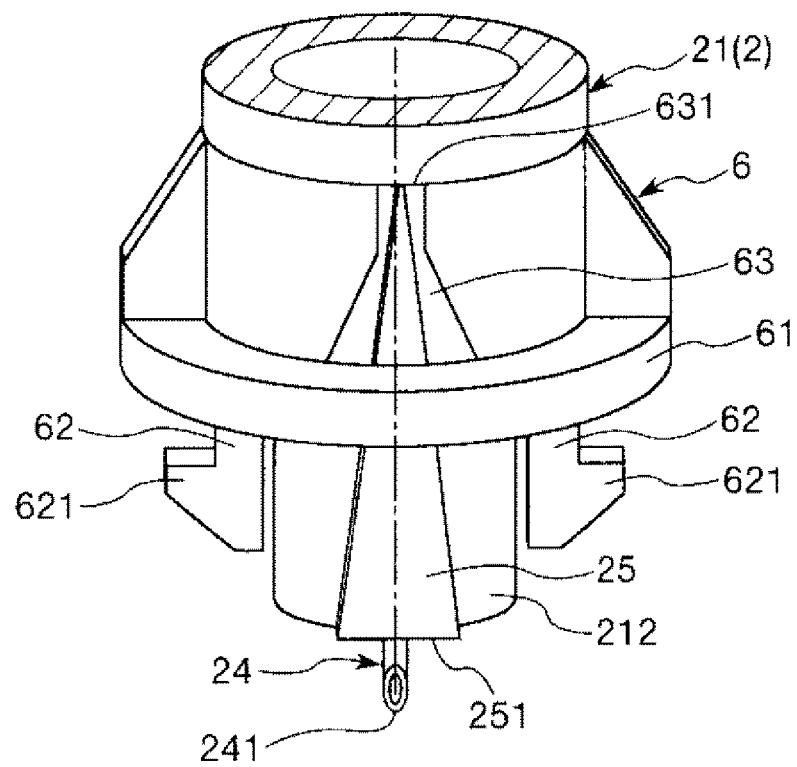
FIG. 8 is a view illustrating a positional relation between the main body and the regulating member (view illustrating the positional relation while the liquid injector is inserted).
Figure 9:
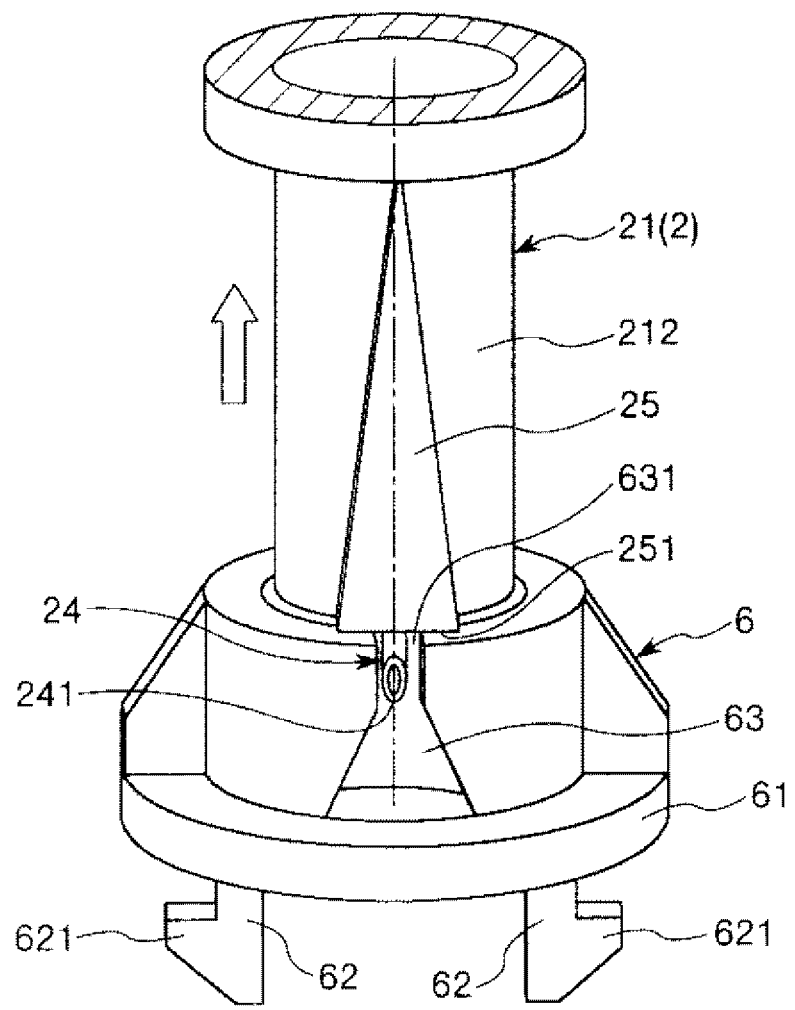
FIG. 9 is a view illustrating a positional relation between the main body and the regulating member illustrated in FIG. 7 (view illustrating the positional relation after finishing the insertion of the liquid injector).

FIGS. 1 to 6 are longitudinal sectional views illustrating using states of the present liquid injector in order according to the present invention, FIG. 7 is an exploded perspective view illustrating a main body and a regulating member in the liquid injector illustrated in FIGS. 1 to 6, and FIGS. 8 and 9 are views illustrating positional relations between the main body and the regulating member illustrated in FIG. 7 (FIG. 8 illustrates the positional relation while the liquid injector is inserted, and FIG. 9 illustrates the positional relation after finishing insertion of the liquid injector). Incidentally, in the following, the upper side in FIGS. 1 to 9 will be referred to as "proximal end" and the lower side therein referred to as "distal end" for convenience of description.

As illustrated in FIGS. 1 to 6, a liquid injector 1 is a prefilled syringe in which medicinal solution (liquid) 100 is preliminarily charged inside, and capable of administering the medicinal solution 100 into a living body. The medicinal solution 100 is not particularly limited, but examples include protein medicinal drug such as antibodies, peptide medicinal drug such as hormones, nucleic acid medicinal drug, cell medicinal drug, blood preparations, vaccines for prevention of various infectious diseases, carcinostatic agents, anesthetics, narcotic drugs, antibiotics, steroid preparations, protease inhibitor, heparin, saccharide injections such as glucose, electrolyte correction injections such as sodium chloride and potassium lactate, vitamin preparations, lipid emulsions, and contrast media.

The liquid injector 1 includes an inner structure body 2, a living body contact member 3, a gripping member 4, a coil spring 5, a regulating member 6, and a cap 7. Now, configuration of each of the components will be described below.

The inner structure body 2 includes a tube body 21 as a main body of the inner structure body, a gasket 22 slidable inside the tube body 21, a pusher 23 that moves and controls the gasket 22 and a hollow needle 24 disposed at a distal-end portion of the tube body 21.

The tube body 21 includes a barrel section 211 having a bottomed tubular shape, and a mouth section 212 formed on a bottom portion of the barrel section 211 in a projecting manner.

An internal cavity of the barrel section 211, more specifically, a space surrounded by the barrel section 211 and the gasket 22 can contain the medicinal solution 100. Further, a flange portion 213 having an enlarged outer diameter is formed on a proximal-end outer peripheral portion of the barrel section 211 in a projecting manner.

The mouth section 212 has a diameter shorter than the barrel section 211, and the medicinal solution 100 is discharged from the mouth section. As illustrated in FIGS. 7 to 9, a wedge portion 25 is formed on an outer peripheral portion of the mouth section 212 in a projecting manner. The wedge portion 25 is formed like a wedge having a width gradually increasing in the distal-end direction from the side view, more specifically, formed in an isosceles triangle according to the present embodiment.

Further, a flange portion 214 having an enlarged outer diameter is formed on a boundary portion between the barrel section 211 and the mouth section 212 in a projecting manner.

The material constituting the tube body 21 is not specifically limited. Examples may be various kinds of following resins: polyesters such as polyvinyl chloride polyethylene, polypropylene, cyclic polyolefin, polystyrene, poly-(4-methylpentene-1), polycarbonate, acrylic resin, acrylonitrile-butadiene-styrene copolymer, polyethylene terephthalate, and polyethylene naphthalate; butadiene-styrene copolymer; and polyamide (e.g., nylon 6, nylon 6.6, nylon 6.10, nylon 12). Among the examples, resin such as polypropylene, cyclic polyolefin, polyesters and poly-(4-methylpentene-1) may be preferable in the view point that these resins are easy to be molded.

The gasket 22 is an elastic body formed of a cylindrically-shaped member. An outer peripheral surface of the gasket 22 closely contacts and slides on an inner peripheral surface of the barrel section 211 of the tube body 21, thereby achieving to push out the medicinal solution 100 from the mouth section 212 while stably keeping liquid tightness inside the barrel section 211.

The material constituting the gasket 22 is not specifically limited, but examples may include various rubber materials such as natural rubber, butyl rubber, isoprene rubber, butadiene rubber, styrene-butadiene rubber, and silicone rubber; various thermoplastic elastomers based on polyurethane, polyester, polyamide, olefin, and styrene; or an elastic material such as combination thereof.

A proximal-end portion of the gasket is connected to the pusher 23 formed elongate.

A finger pad 231 having an enlarged outer diameter is formed on a proximal-end portion of the pusher 23. When executing pushing operation for the pusher 23, a thumb, for example, is placed on the finger pad 231, thereby achieving to execute the pushing operation. With the pushing operation, the gasket 22 is advanced and the medicinal solution 100 can be pushed out from the mouth section 212.

A projected portion 232 is formed halfway in longitudinal direction of the pusher 23 in a projecting manner. The projected portion 232 is formed in a ring shape along an outer peripheral direction of the pusher 23.

The material constituting the pusher 23 is not particularly limited, and for example, the pusher may be formed of the same material as the tube body 21.

The hollow needle 24 as an intradermal needle is engaged and mounted on the mouth section 212 of the tube body 21. Further, the hollow needle 24 is in communication with the barrel section 211 via the mouth section 212.

The hollow needle 24 includes a sharp needle tip 241 at the tip thereof. The living body surface 200 can be punctured with the needle tip 241 (see FIG. 4). While puncture, the medicinal solution 100 can be injected into the living body (see FIG. 5).

The hollow needle 24 is formed of, for example, metallic material such as stainless steel, aluminum, aluminum alloy, titanium, or titanium alloy.

Figure 1:
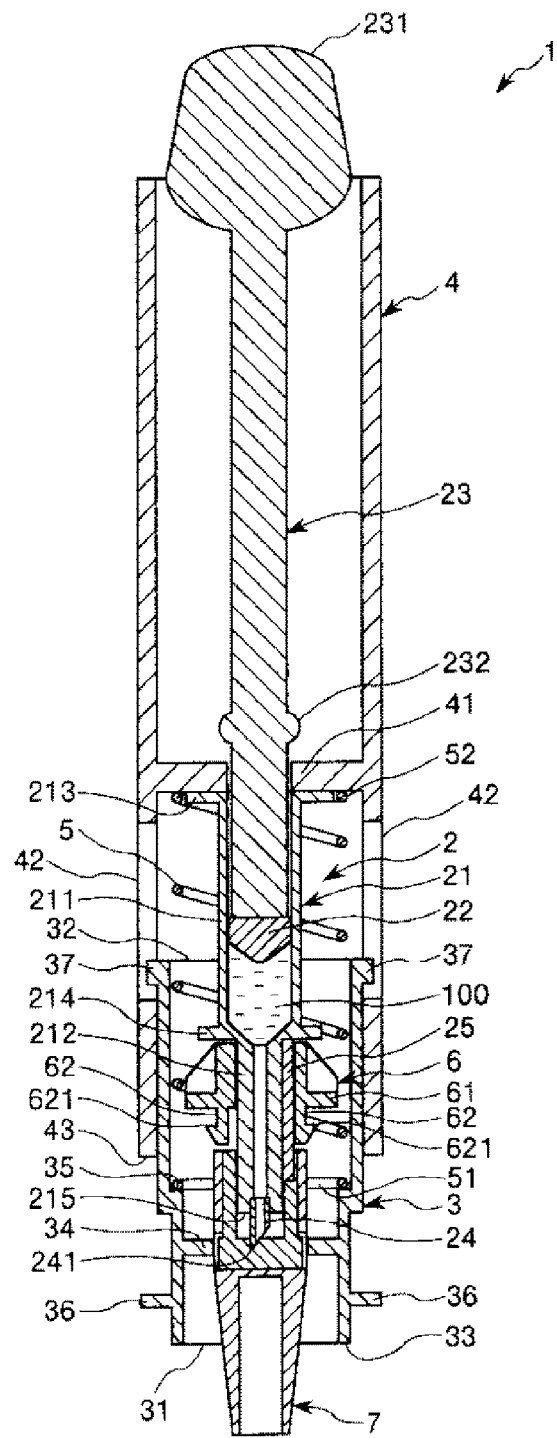
FIG. 1 is a longitudinal sectional view illustrating a using state of a liquid injector in order according to the present invention.

Also, as illustrated in FIG. 1, when the liquid injector 1 is unused, the hollow needle 24 is covered with a cap 7. The cap 7 is formed cylindrical, and detachably attached to the mouth section 212 of the tube body 21.

The inner structure body 2 configured as described above is disposed on the inner side of the living body contact member 3 concentrically with the living body contact member 3.

The living body contact member 3 includes distal-end opening 31 opened at the distal end and a tube body having a proximal-end opening 32 opened at the proximal end. Further, an edge portion of the distal-end opening 31 functions as a pad 33 to be placed on living body surface 200 (FIGS. 2 to 6).

Figure 2:
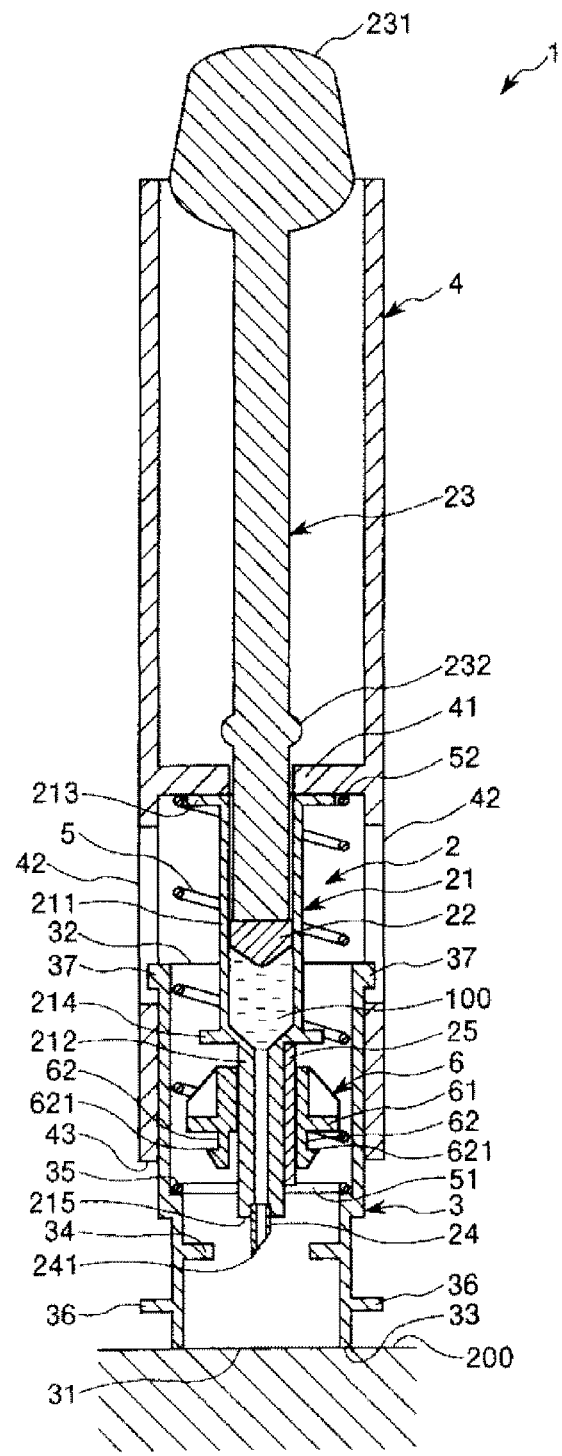
FIG. 2 is a longitudinal sectional view illustrating the using state of the liquid injector in order according to the present invention.
Figure 3:
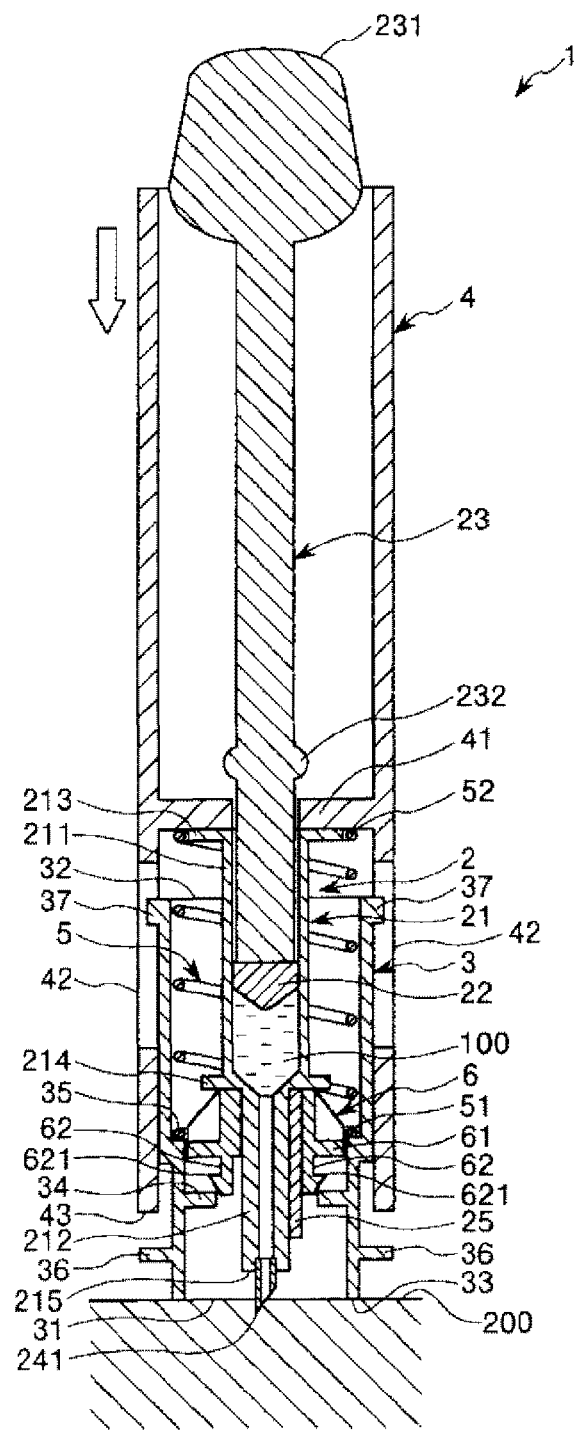
FIG. 3 is a longitudinal sectional view illustrating the using state of the liquid injector in order according to the present invention.
Figure 4:
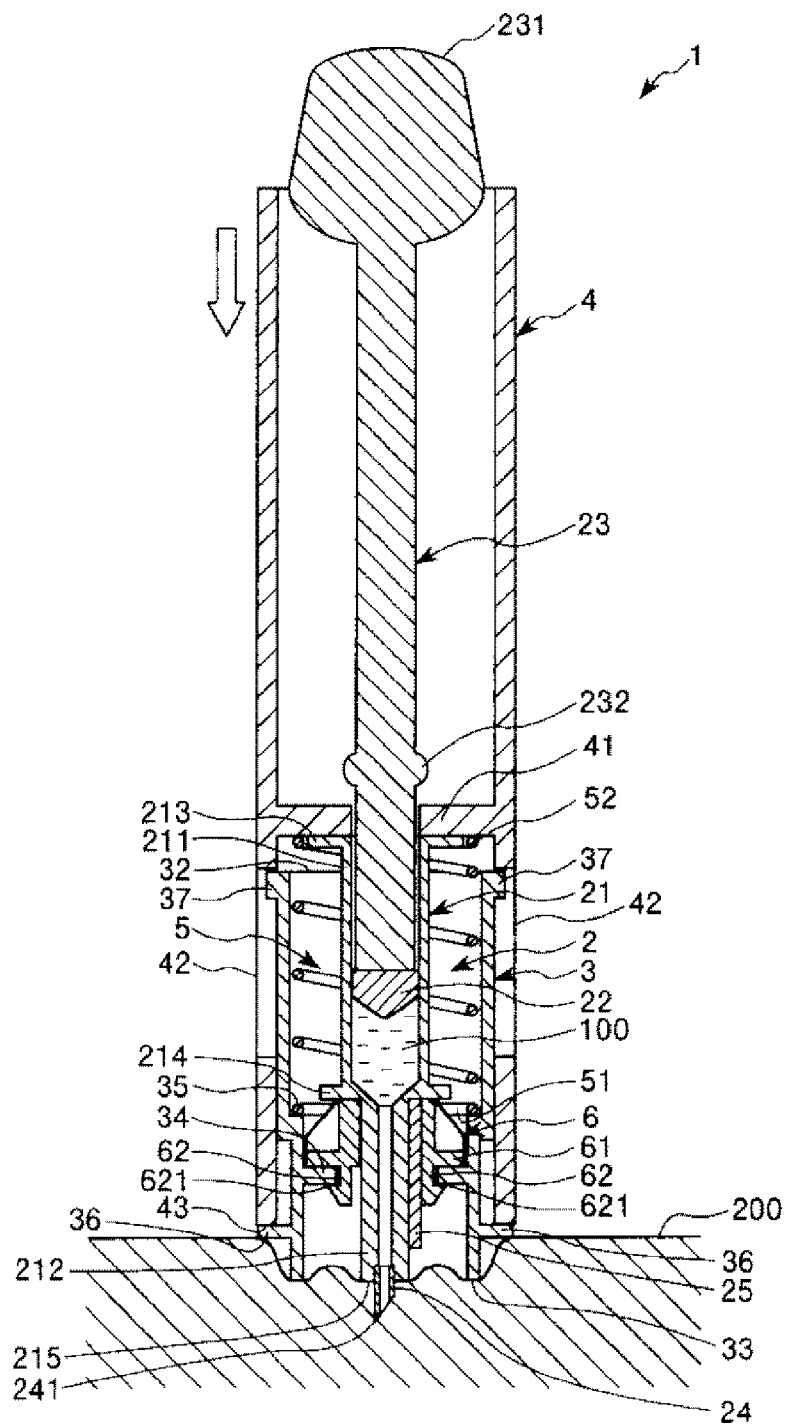
FIG. 4 is a longitudinal sectional view illustrating the using state of the liquid injector in order according to the present invention.

Additionally, while the pad 33 of living body contact member 3 is placed on the living body surface 200, the inner structure body 2 can move to a first position where the needle tip 241 is located closer to the proximal-end side than the distal-end opening 31 (see FIGS. 1, 2, and 6) and a second position where the needle tip 241 is more projected to the distal-end side than the distal-end opening 31 and inserted into the living body surface 200 (see FIGS. 3 to 5).

An engagement portion (projected portion) 34 is formed halfway in axial direction of living body contact member 3 in a projecting manner from an inner peripheral portion. The engagement portion 34 is formed in a ring shape on an inner peripheral portion of the living body contact member 3 along a circumferential direction. As illustrated in FIG. 4, the engagement portion 34 can be engaged with the regulating member 6 when the inner structure body 2 moves to the second position.

Further, on the inner peripheral portion of the living body contact member 3, a stepped section 35 having an outer diameter gradually changing is formed more on the proximal-end side than the engagement portion 34. The stepped section 35 functions as a spring seat on which a distal end 51 of the coil spring 5 abuts.

On the outer peripheral portion of the living body contact member 3, pairs of stoppers 36, 37 each including a protrusion are respectively formed on the distal-end side portion and proximal-end side portion of the living body contact member in a projecting manner. As illustrated in FIGS. 4 and 5, the stopper 36 abuts on a distal end 43 of the gripping member 4 to be gripped when the inner structure body 2 is moved and controlled, thereby achieving to regulate a movement limit of the inner structure body 2. As illustrated in FIGS. 1, 2 and 6, the stopper 37 abuts on an edge portion of a slit 42 formed on a wall portion (tube wall) of the gripping member 4, thereby achieving to prevent the living body contact member 3 from separating from the gripping member 4.

The cylindrical gripping member 4 is disposed concentrically with the living body contact member 3 on the more outer peripheral side than the living body contact member 3. The gripping member 4 supports the inner structure body 2 movable with respect to the living body contact member 3, and is gripped when the inner structure body 2 is moved and controlled.

A supporting portion 41 that supports the inner structure body 2 is disposed halfway in the axial direction of the gripping member 4. The supporting portion 41 is formed on the inner peripheral portion of the gripping member 4 in a projecting manner. Also, the supporting portion 41 is formed in a ring shape along the circumferential direction of the inner peripheral portion of the gripping member 4. Further, a flange portion 213 of the tube body 21 of the inner structure body 2 is supported and fixed at a distal-end surface of the supporting portion 41 thus configured. This fixing method is not particularly limited, and exemplary methods may include adhesion (adhesion with an adhesive or solvent) and welding (such as thermal welding, high frequency welding, and ultrasonic welding).

Additionally, on the gripping member 4, a pair of slits 42 penetrating the wall portion is formed on a position more on the distal-end side than the supporting portion 41. The pair of slits 42 is disposed facing each other via a center axis of the gripping member 4. Each of the stoppers 37 of the living body contact member 3 can move each of the slits 42, and the living body contact member 3 can be prevented from separating from the gripping member 4 by the stopper 37 abutting on an edge portion on the distal-end side of the slit 42.

The material constituting the living body contact member 3, gripping member 4 and regulating member 6 is not particularly limited, and examples may be the same materials for the tube body 21.

Inside the gripping member 4, the coil spring 5 formed of, for example, stainless steel is disposed being compressed. The coil spring 5 is a biasing member configured to bias the inner structure body 2 in the proximal-end direction. As described above, the distal end 51 of the coil spring 5 abuts on the stepped section 35 of the living body contact member 3. On the other hand, a proximal end 52 of the coil spring 5 abuts on the supporting portion 41 of the gripping member 4. With this configuration, the inner structure body 2 can be biased in the proximal-end direction via the gripping member 4.

The regulating member 6 is detachably mounted on the mouth section 212 of the tube body 21 of the inner structure body 2. After use, more specifically, after finishing puncture, the regulating member 6 regulates excessive entry of the fingertip or the like to the inside of the liquid injector 1 from the distal-end side, and also regulates the inner structure body 2 so as not to move again in the distal-end direction (see FIG. 6).

As illustrated in FIG. 7, the regulating member 6 is formed of a ring-shaped member. With this configuration, the regulating member 6 can be engaged with the outer peripheral portion of the mouth section 212 of the tube body 21, and can be detachably attached to the mouth section 212. Note that the regulating member 6 can be movable together with the inner structure body 2 while being attached to the inner structure body 2.

A flange portion 61 having an enlarged outer diameter is formed on the outer peripheral portion of the regulating member 6 in a projecting manner. The flange portion 61 is formed on the outer peripheral portion of the regulating member 6 along the circumferential direction.

Further, on the regulating member 6, a pair of projecting pieces 62 projecting downward is formed more on the distal-end side than the flange portion 61. The pair of projecting pieces 62 is disposed facing each other via a center axis of the regulating member 6. Further, on the distal-end portion of the respective projecting pieces 62, claws 621 projecting outward, more specifically, the claws projecting in directions opposing each other are formed.

As illustrated in FIG. 4, when the inner structure body 2 is moved from the first position to the second position, the regulating member 6 can grip the plate-like shaped projected portion 34 of the living body contact member 3 from the both sides (distal-end side and proximal-end side) between the flange portion 61 and each of the claws 621 of the respective projecting pieces 62 at the second position. In this manner, the regulating member 6 is fixed with the living body contact member 3. Thus, it can be said that the flange portion 61 and the claws 621 of respective the projecting pieces 62 function as fixing portions whereby the regulating member 6 is fixed to the living body contact member 3 at the second position.

Further, as illustrated in FIG. 6, when the inner structure body 2 returns to the first position from this fixed state, the regulating member 6 does not moves together with the inner structure body 2. Rather, because the regulating member 6 is fixed to the living body contact member 3, the regulating member 6 separates from the inner structure body 2 and stays where it is.

The regulating member 6 thus staying may cover the distal-end opening 31 of the living body contact member 3 in a ring shape on the slightly more proximal-end side than the living body contact member. With this configuration, even in the case where the operator's fingertip enters the inside, for example, from the distal-end opening 31 of the living body contact member 3 when the liquid injector 1 is separated from the living body surface 200, the regulating member 6 regulates further entry of the fingertip, more specifically, prevents the fingertip from reaching the needle tip 241 of the inner structure body 2. Accordingly, it is possible to surely prevent erroneous puncture with the needle tip 241 of the hollow needle 24 to the fingertip. Therefore, the liquid injector 1 is improved to have excellent safety after use.

Incidentally, an inner diameter $\phi d$ of the regulating member 6 is a size enough to regulate entry of the fingertip, for example, preferably 6 to 17 mm, and more preferably 8 to 13 mm. By setting the inner diameter $\phi d$ of the regulating member 6 to the above-described size, entry of the fingertip can be surely regulated and also erroneous puncture to the fingertip can be surely prevented.

Additionally, as described above, in the case where the distal-end opening 31 of the living body contact member 3 is covered with the regulating member 6, it is possible to prevent the fingertip from reaching the needle tip 241 of the inner structure body 2 even when a retracting amount (moved amount from the second position to the first position) of the inner structure body 2 is relatively small, more specifically, even without excessively moving the inner structure body 2 far inside (proximal-end side). This minimizes an amount of extension of the coil spring 5 when the inner structure body 2 is moved to the proximal-end direction, thereby achieving to reduce the size of the liquid injector 1. Moreover, pushing force against the biasing force of the coil spring 5 can be reduced at the time of puncture, thereby improving operability of the liquid injector 1.

As illustrated in FIG. 7, a discontinuous portion 63 is formed on the ring-shaped wall portion of the regulating member 6. The discontinuous portion 63 has a width gradually increasing in distal-end direction along the circumferential direction of regulating member 6, in the same manner as the wedge portion 25 of the inner structure body 2. Note that the width of a minimum width portion 631 located at the most proximal end of the discontinuous portion 63 is smaller than the width of a maximum width portion 251 located at the most distal end of the wedge portion 25.

As illustrated in FIGS. 8 and 9, when the inner structure body 2 positioned at the second position is returned to the first position again, the wedge portion 25 of the inner structure body 2 can pass the discontinuous portion 63 of the regulating member 6 together with the returning movement. On the other hand, by contrast, when the inner structure body 2 having returned to the first position tries to return to the second position again, the maximum width portion 251 of the wedge portion 25 of the inner structure body 2 is prevented from entering the minimum width portion 631 of the discontinuous portion 63 of the regulating member 6. As a result, the wedge portion 25 is inhibited from passing the discontinuous portion 63. In this manner, the inner structure body 2 having returned to the first position can be surely regulated so as not to move again to the second position. Accordingly, the hollow needle 24 of the inner structure body 2 can be surely prevented from involuntarily projecting outside.

Thus, in the liquid injector 1, erroneous puncture to the fingertip with the hollow needle 24 after use can be surely prevented by the following synergistic effects: preventing the fingertip from entering the liquid injector 1 and regulating the inner structure body 2 not to move again in the distal-end direction.

Next, an exemplary use method of the liquid injector 1 will be described with reference to FIGS. 1 to 6.

[1] An unused liquid injector 1 is prepared as illustrated in FIG. 1. Since the cap 7 is attached to the liquid injector 1, the cap 7 is removed at the time of use.

[2] Next, the gripping member 4 of the liquid injector 1 is gripped with one hand, and the pad 33 of the living body contact member 3 of the liquid injector 1 is placed on a target region of the living body surface 200 to be punctured, as illustrated in FIG. 2.

[3] Then, from the state illustrated in FIG. 2, the entire liquid injector 1 is pushed toward the living body surface 200 against the biasing force of the coil spring 5 as illustrated in FIG. 3. This pushing operation can be easily executed by gripping the gripping member 4.

Further, by the pushing operation, the force is transmitted to the inner structure body 2 via the supporting portion 41 of the gripping member 4, thereby starting to move the inner structure body 2 from the first position to the second position together with the regulating member 6.

[4] Then, the pushing operation is continued until the distal end 43 of the gripping member 4 abuts on the stopper 36 of the living body contact member 3, as illustrated in FIG. 4. In this manner, the inner structure body 2 moves to the second position, and the living body surface 200 can be punctured with the hollow needle 24.

Note that, at this point, the pad 33 (distal-end surface) of the living body contact member 3 is positioned substantially in the same plane as the distal-end surface 215 of the mouth section 212 of the tube body 21 in the liquid injector 1. Further, the hollow needle 24 is orthogonal to the plane formed with the pad 33 of the living body contact member 3 and the distal-end surface 215 of the tube body 21.

Therefore, as illustrated in FIG. 4, in the case where the living body surface 200 is punctured with the hollow needle 24, the distal-end surface 215 of the tube body 21 contacts the living body surface 200, and at the same time the pad 33 of the living body contact member 3 contacts a skin surface. With this configuration, the hollow needle 24 can be supported substantially orthogonal to the living body surface 200 by the living body contact member 3. As a result, the hollow needle 24 is prevented from wobbling, and the hollow needle 24 can be inserted straightly into the living body surface 200.

Incidentally, the distal-end surface 215 of the tube body 21 is not necessarily positioned at the same plane as the pad 33 of the living body contact member 3. In other words, the distal-end surface 215 of the tube body 21 may be positioned on the proximal-end side in the axial direction of the living body contact member 3 from the pad 33.

Also, as described above, the flange portion 61 and the claws 621 of respective projecting pieces 62 grip the projected portion 34 of the living body contact member 3, and the regulating member 6 is fixed to the living body contact member 3 at this point.

[5] Next, from the state illustrated in FIG. 4, the thumb of the hand that has gripped the gripping member 4 is placed on the finger pad 231 of the pusher 23 of the inner structure body 2, and the pusher 23 is pushed by the thumb as illustrated in FIG. 5. In this matter, the medicinal solution 100 is pushed out from the mouth section 212 of the inner structure body 2 and administered to the inside of the living body through the hollow needle 24.

[6] Next, when the pushing force against the liquid injector 1 is released, the inner structure body 2 is correspondingly pushed up by the biasing force of the coil spring 5 together with the gripping member 4, and returns again to the first position. Also, when the inner structure body 2 returns again to the first position, the regulating member 6 is fixed to the living body contact member 3, and therefore can be separated from the inner structure body 2.

After that, the liquid injector 1 is separated from the living body surface 200. At this point, as described above, the distal-end opening 31 of the living body contact member 3 is covered with the regulating member 6, and therefore the operator's finger or the like is prevented from involuntarily entering from the distal-end opening 31 of the living body contact member 3. As a result, erroneous puncture to the operator's finger or the like with the hollow needle 24 can be surely prevented. Also, the regulating member 6 surely prevents the inner structure body 2 having returned to the first position from moving again to the second position, and also prevents the hollow needle 24 from involuntarily projecting outside. This also surely prevents the erroneous puncture to the operator's finger or the like.

While the liquid injector according to the embodiment of the present invention illustrated in the attached drawings has been described above, the present invention is not limited thereto, and each of the components of the liquid injector can be replaced with a constituent element that can exhibit an equivalent function. Further, arbitrary constituent elements may be added.

Further, according to the above embodiment, the regulating member is configured to cover a part of the distal-end opening of the living body contact member at the moved place, but the configuration is not limited thereto, and the regulating member may be configured to cover an entire part of distal-end opening 31, for example.

Also, the regulating member may be housed in a tub or next conforming to the ISO Standard by reducing the inner diameter of the restricting member.

Industrial Applicability

The liquid injector according to embodiments of the present invention includes: a living body contact member formed of a tube body including an opening opened at a distal end and having an edge portion of the opening placed on a living body surface; an inner structure body including: a main body disposed inside the living body contact member, formed cylindrical, and having an internal cavity filled with liquid; and a hollow needle disposed on a distal-end portion of the main body, communicating with the main body and including a sharp needle tip at the end, wherein the inner structure body is supported movably to a first position where the needle tip is located closer to the proximal-end side than the opening and to a second position where the needle tip is projected more to the distal-end side than the opening to puncture a living body surface while the living body contact member is placed on the living body surface; and a regulating member detachably mounted on the inner structure body, movable together with the inner structure body in the mounted state, and including a fixing portion to be fixed to the living body contact member at the second position. When the inner structure body moves to the second position from the first position and returns to the first position again, the regulating member is fixed to the living body contact member with the fixing portion at the second position, simultaneously separated from the inner structure body, and stays at the position to cover at least a part of the vicinity of the opening.

Moreover, according to the present invention, the vicinity of the opening of the living body contact member can be surely covered with the regulating member. With this configuration, in the case where an operator's fingertip (finger or the like), for example, enters the inside from the opening of the living body contact member when the liquid injector is separated from the living body surface after puncture, entry of the fingertip can be regulated by the regulating member. Accordingly, erroneous puncture to the fingertip with the needle tip of the hollow needle can be surely prevented. Therefore, the liquid injector according to embodiments of the present invention is excellent in safety after use and has industrial applicability.

What is claimed is:

1. A liquid injector comprising:
   a contact member comprising a tube body including an opening located at a distal end of the contact member, an edge portion around the opening being configured to be placed on a living body surface;
   an inner structure body comprising:
   a cylindrical main body disposed inside the contact member, the cylindrical main body having an internal cavity configured to be filled with liquid; and
   a hollow needle disposed on a distal-end portion of the main body, the hollow needle communicating with the main body and including a sharp needle tip at a distal end of the hollow needle,
   wherein the inner structure body is movable to (i) a first position at which the needle tip is located proximal of the opening, and (ii) a second position at which the needle tip is located distal of the opening so as to be configured to puncture the living body surface while the body contact member is placed on the living body surface; and
   a regulating member detachably mounted on the inner structure body, movable together with the inner structure body in the mounted state, and including a fixing portion to be fixed to the contact member at the second position,
   wherein, when the inner structure body moves to the second position from the first position and returns to the first position again, the regulating member is fixed to the contact member with the fixing portion at the second position, separated from the inner structure body, and stays at a position at which the regulating member covers at least part of an area of the opening, and
   wherein the regulating member is configured such that the inner structure body that has returned again to the first position is inhibited from moving again to the second position.

2. The liquid injector according to claim 1, wherein the regulating member covers at least a part of an area of the opening at a location proximal of the opening.

3. The liquid injector according to claim 1, wherein the regulating member is formed in a ring shape and an inner diameter of the regulating member is sized to inhibit entry of a fingertip.

4. The liquid injector according to claim 1, wherein:
   the contact member includes a projected portion that projects from an inner peripheral portion of the contact member, and
   the fixing portion is configured to grip the projected portion from a distal side and a proximal side of the projected portion.

5. The liquid injector according to claim 1, wherein:
   the main body includes a wedge portion that projects from an outer peripheral portion of the main body and has a width that gradually increases in the distal direction in a side view, and
   the regulating member is formed in a ring shape and having a wall portion on which a discontinuous portion is formed and the discontinuous portion allows the wedge portion to pass in a direction to the first position when the inner structure body returns again to the first position while the discontinuous portion inhibits the wedge portion from passing in an opposite direction.

6. The liquid injector according to claim 1, wherein the inner structure body includes a gasket that is slidable inside the main body and a pusher connected to the gasket and configured to move the gasket.

7. The liquid injector according to claim 1, further comprising a gripping member which is disposed on an outer peripheral side of the inner structure body and configured to be gripped when the inner structure body is moved.

8. The liquid injector according to claim 1, further comprising a biasing member configured to bias the inner structure body in a proximal direction.

9. A liquid injector comprising:
a contact member comprising a tube body including an opening located at a distal end of the contact member, an edge portion around the opening being configured to be placed on a living body surface;
an inner structure body comprising:
    a cylindrical main body disposed inside the contact member, the cylindrical main body having an internal cavity configured to be filled with liquid; and
    a hollow needle disposed on a distal-end portion of the main body, the hollow needle communicating with the main body and including a sharp needle tip at a distal end of the hollow needle,
    wherein the inner structure body is movable to (i) a first position at which the needle tip is located proximal of the opening, and (ii) a second position at which the needle tip is located distal of the opening so as to be configured to puncture the living body surface while the body contact member is placed on the living body surface; and
a regulating member detachably mounted on the inner structure body, movable together with the inner structure body in the mounted state, and including a fixing portion to be fixed to the contact member at the second position,
wherein, when the inner structure body moves to the second position from the first position and returns to the first position again, the regulating member is fixed to the contact member with the fixing portion at the second position, separated from the inner structure body, and stays at a position at which the regulating member covers at least part of an area of the opening,
wherein the main body includes a wedge portion that projects from an outer peripheral portion of the main body and has a width that gradually increases in the distal direction in a side view, and
wherein the regulating member is formed in a ring shape and having a wall portion on which a discontinuous portion is formed and the discontinuous portion allows the wedge portion to pass in a direction to the first position when the inner structure body returns again to the first position while the discontinuous portion inhibits the wedge portion from passing in an opposite direction.

10. The liquid injector according to claim 9, wherein the regulating member covers at least a part of an area of the opening at a location proximal of the opening.

11. The liquid injector according to claim 9, wherein the regulating member is formed in a ring shape and an inner diameter of the regulating member is sized to inhibit entry of a fingertip.

12. The liquid injector according to claim 9, wherein:
the contact member includes a projected portion that projects from an inner peripheral portion of the contact member, and
the fixing portion is configured to grip the projected portion from a distal side and a proximal side of the projected portion.

13. The liquid injector according to claim 9, wherein the inner structure body includes a gasket that is slidable inside the main body and a pusher connected to the gasket and configured to move the gasket.

14. The liquid injector according to claim 9, further comprising a gripping member which is disposed on an outer peripheral side of the inner structure body and configured to be gripped when the inner structure body is moved.

15. The liquid injector according to claim 9, further comprising a biasing member configured to bias the inner structure body in a proximal direction.

* * * * *